United States Patent [19]

Koishi

[11] Patent Number: 5,043,584
[45] Date of Patent: Aug. 27, 1991

[54] PHOTON-COUNTING TYPE STREAK CAMERA DEVICE

[75] Inventor: Musubu Koishi, Shizuoka, Japan

[73] Assignee: Hamamatsu Photonics K.K., Shizuoka, Japan

[21] Appl. No.: 488,861

[22] Filed: Mar. 5, 1990

[30] Foreign Application Priority Data

Mar. 8, 1989 [JP] Japan .................................. 1-55530

[51] Int. Cl.$^5$ ................................................ G01J 5/02
[52] U.S. Cl. ............................ 250/458.1; 250/213 VT
[58] Field of Search ............. 250/458.1, 347, 213 VT; 358/209, 217

[56] References Cited

U.S. PATENT DOCUMENTS 4,740,685  4/1988  Koishi .......................... 250/213 VT
4,797,747  1/1989  Takiguchi et al. ....... 250/213 VT X
4,902,135  2/1990  Takiguchi ........................... 356/373
4,958,231  9/1990  Tsuchiya ............................. 358/211
4,967,080  10/1990 Urakami et al. ................... 250/336.1

FOREIGN PATENT DOCUMENTS 59-58745  4/1984  Japan .
SU905915  2/1982  U.S.S.R. ........................ 250/213 VT

OTHER PUBLICATIONS

Stavola et al., "Picosecond Time Delay Fluorimetry Using A Jitter-Free Streak Camera", Optical Communications, vol. 34, No. 3 (Sep. 1980).
Tsuchiya, Y. et al., "Photon-Counting Image Acquisition System And Its Applications", Journal of Imaging Technology, vol. 11, No. 5, Oct. 1985, pp. 215–220.
Tsuchiya, Y., "Advances in Streak Camera Instrumentation for the Study of Biological and Physical Processes", Reprinted from IEEE Journal of Quantum Electronics, vol. QE-20, No. 12, 12/84, pp. 1516–1528.
Inuzuka, E. et al., "Solid State Imaging Arrays", vol. 570, Aug. 22–23, 1985, pp. 111–118.
Urakami, T. et al., "High Speed Photography, Videography, and Photonics IV", vol. 693, Aug. 19–20, 1986, pp. 98–104.
Journal of the Institute of Television Engineers of Japan, vol. 36, No. 11, pp. 1010–1012.

Primary Examiner—Constantine Hannaher
Assistant Examiner—Jacob M. Eisenberg
Attorney, Agent, or Firm—Finnegan, Henderson, Farabow, Garrett & Dunner

[57] ABSTRACT

A photon-counting type streak camera device measures by an integration operation the probability distribution of production timing of phenomenon light such as fluorescence light which a specimen produces upon reception of repeatedly generated pulse exciting light. A phenomenon streak camera system time-measures the phenomenon light, and a reference streak camera system time-measures reference light being synchronous with the exciting light. An arithmetic unit calculates the difference between outputs of the phenomenon and reference streak camera systems, so that the streak camera device can be prevented from being effected by a jitter or drift caused by a power change of a pulse light source.

7 Claims, 6 Drawing Sheets

TRIGGER PULSE BEAM

OUTPUT OF PHOTODETECTOR

OUTPUT OF TRIGGER CIRCUIT

SWEEP VOLTAGE

FLUORESCENT LIGHT

PHOTON-COUNTING TYPE STREAK CAMERA DEVICE

BACKGROUND OF THE INVENTION

This invention relates to streak camera devices, and more particularly to a streak camera device of photon-counting type.

Conventional techniques of observing a weak ultra-high-speed optical phenomena have been disclosed, for instance, by Japanese Patent Application Unexamined Publication No. 58745/1984, U.S. Pat. No. 4,797,747 assigned to the present assignee, and the Journal of the Institute of Television Engineers of Japan, Vol. 36, No. 11, pp. 1010–1012 (1982).

A photon-counting type streak camera device according to the above conventional techniques is as shown in FIG. 6.

As shown in FIG. 6, a pulse light source 1 comprising a mode-locked dye laser generates a pulse laser beam LB, which is split by a half-mirror HM into an exciting pulse beam $LB_1$ and a trigger pulse beam $LB_2$. The exciting pulse beam $LB_1$ is reflected by mirrors in an optical delay section, so that it is applied to a specimen 3. As a result, the specimen 3 produces fluorescence light FL.

The fluorescence light FL passed through a slit $S_1$ is focused on the photocathode 41 of a streak tube 4 by a lens $L_1$, whereupon the photocathode 41 emits photoelectrons EB. The photoelectrons EB thus emitted pass through a grid 42, are accelerated by an accelerating electrode 43, and deflected by deflecting electrodes 44, so that they are applied to a microchannel plate (MCP) 45, where they are subjected to electron multiplication. The multiplied electrons are applied to a phosphor screen 46, thus forming a streak image 47.

On the other hand, the trigger pulse beam $LB_2$ from the half-mirror HM is detected by a photodetector 5, and is applied through a variable delay circuit 6 to a trigger circuit 7, whereby a trigger signal is produced and applied to a sweep circuit 8. The timing of applying the exciting pulse beam $LB_1$ to the specimen 3 and the timing of the trigger signal being outputted by the trigger circuit 7 are held in a certain relation by the optical delay section 2 and the variable delay circuit 6. Therefore, the position of the streak image 47 formed on the phosphor screen 46 corresponds to the period of time which elapses from the time instant when the exciting pulse beam $LB_1$ is applied to the specimen 3 until the fluorescence light FL is generated. The streak image of the fluorescence light FL is formed on the phosphor screen 46 by illuminating the specimen 3 by the exciting pulse beam $LB_1$, focusing the generated fluorescent light FL on the photocathode 41, and sweeping the photoelectrons EB. This operation is performed repeatedly, so that positions of the streak images 47 on the phosphor screen 46 are integrated. As a result, the weak high-speed optical phenomenon can be measured.

When, in the above-described system, the mode-locked dye laser forming the pulse light source 1 changes in power, then the streak image 47 on the phosphor screen 46 vibrates every sweep; that is, a so-called "jitter phenomenon" occurs. This is due to the following fact: When the laser power changes as indicated by $P_a$ and $P_b$ in FIG. 7(a), the output of the photodetector 5 is changed as indicated by $V_a$ and $V_b$ in FIG. 7(b), whereby the timing of the triggering of the streak camera is shifted as indicated by $TRG_a$ and $TRG_b$, as a result of which the timing of sweeping with respect to the light pulse is changed as indicated by $V_{sa}$ and $V_{sb}$ in FIG. 7(c).

The above-described change of the timing, depending on the quality and adjustment of the laser, causes a jitter of several picoseconds to several tens of picoseconds. On the other hand, even if an ideal trigger signal is obtained with the power of the laser maintained unchanged, the electronic circuit in the streak camera has a jitter of several picoseconds to several tens of picoseconds, and suffers from a so-called "drift", i.e., the change in sweep timing which lasts over a relatively long period of time.

The jitter or drift causes no troubles when an optical phenomenon is measured by a single streak sweep; however, it will limit the time resolution in measurement in the case where it is required to measure a weak optical phenomenon with high S/N ratio by measuring it repeatedly with a time resolution of from several picoseconds to subpicoseconds, and integrating the results of measurement. For instance, in the case of a streak camera having a time resolution of 2 psec, with a jitter of 10 psec the time resolution of the system will be of the order of 11 psec.

SUMMARY OF THE INVENTION

In view of the foregoing, an object of this invention is to provide a photon-counting type streak camera device in which, even when a drift or jitter takes place, the time resolution is maintained unchanged.

The specific feature of a streak camera device according to the invention resides in that a phenomenon streak camera system for time-measuring a phenomenon light beam (such as fluorescence light) which a specimen emits upon reception of an exciting light beam, and a reference streak camera system for time-measuring a reference light beam which is synchronous with the exciting light beam are juxtaposed. More specifically, the streak camera device of the invention comprises: light splitting means for splitting a pulse beam repeated at a predetermined frequency into a reference light beam and an exciting light beam to be applied to the specimen; trigger signal generating means for producing a trigger signal synchronous with the reference light beam; reference streak means for sweeping according to the trigger signal photoelectrons which are produced upon incidence of the reference light beam; phenomenon streak means for sweeping according to the trigger signal photoelectrons which are produced upon incidence of the phenomenon light beam which the specimen emits upon reception of the exciting light beam; reference position detecting means for detecting the time position at which a reference streak image is formed by the reference streak means; phenomenon position detecting means for detecting the time position at which a phenomenon streak image is formed by the phenomenon streak means; and arithmetic means for calculating the timing of production of the phenomenon light beam from the difference between an output of the phenomenon position detecting means and an output of the reference position detecting means.

In the streak camera device of the invention, when a drift or jitter occurs because of the change in power of a pulse light source itself or the change in a light source drive circuit, the phenomenon streak system and the reference streak system are affected thereby in the same manner. Therefore, by obtaining the difference between the resultant effects, the time resolution can be improved greatly.

DETAIlED DESCRIPTION OF THE PREFERRED EMBODIMENTS

Figure 1:
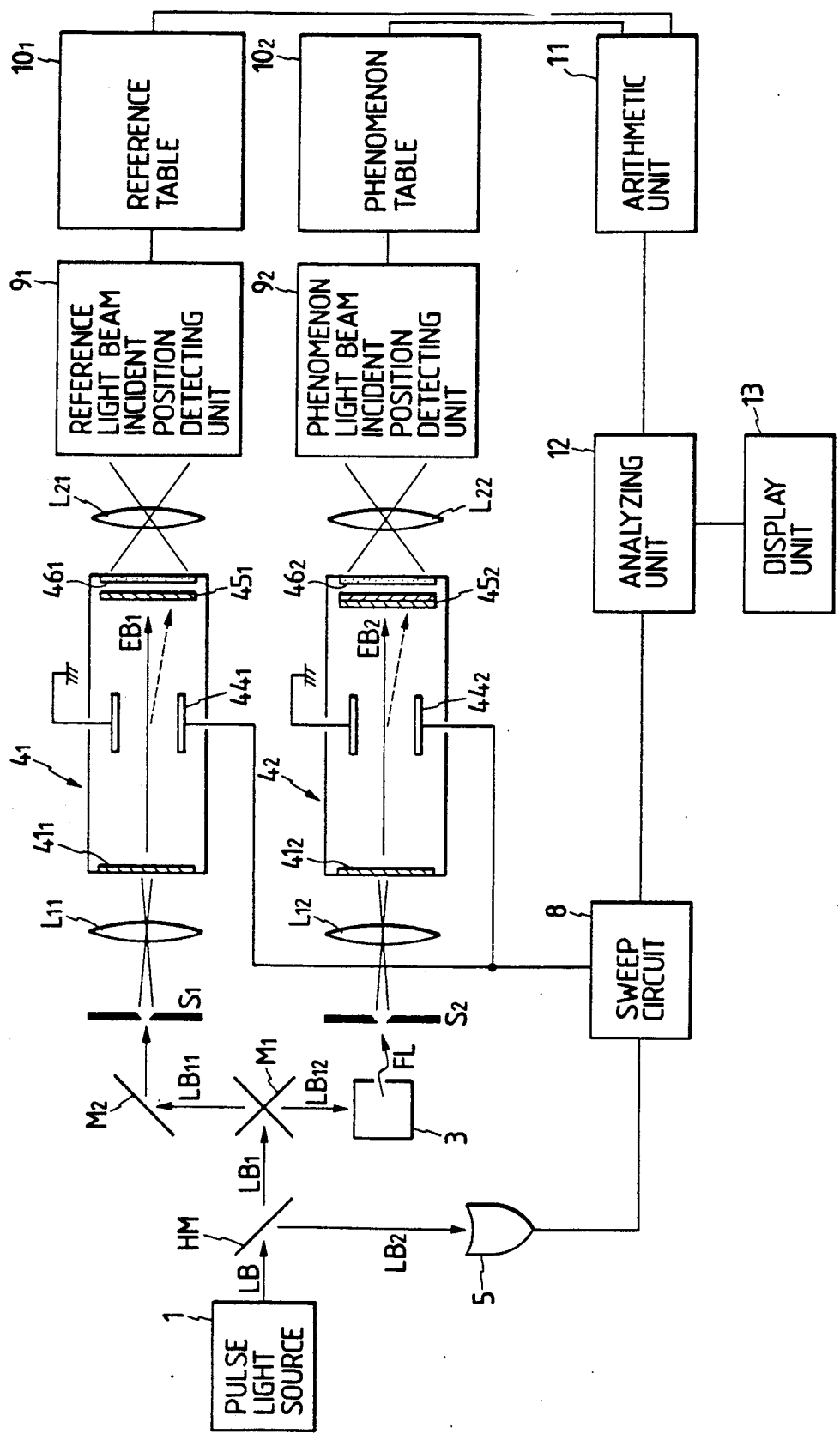
FIG. 1 is an explanatory diagram, partly as a block diagram, showing the arrangement of a streak camera device which is a first embodiment of this invention.

Preferred embodiments of this invention will be described with reference to the accompanying drawings:

FIG. 1 is an explanatory diagram, partly as a block diagram, showing a streak camera device, which is a first embodiment of the invention. As shown in FIG. 1, a pulse light source 1 comprising a mode-locked dye laser or CPM ring laser outputs a pulse laser beam LB, which is split by a half-mirror HM into an exciting pulse beam LB and a trigger pulse beam $LB_2$. The trigger pulse beam $LB_2$ is applied to a photodetector 5 such as a high-speed photodiode, and, similarly as in the conventional streak camera device, a trigger signal is generated and applied to a sweep circuit 8. In FIG. 1, a variable delay circuit 6 and a trigger circuit 7 are not shown. On the other hand, the exciting pulse beam $LB_1$ is reflected and split by a bidirectional mirror $M_1$ into a reference pulse beam $LB_{11}$ and an exciting pulse beam $LB_{12}$. The reference pulse beam is reflected by a mirror $M_2$, passed through a slit $S_1$, and focused by a lens $L_{11}$, thus being applied to the photocathode $41_1$ of a reference streak tube $4_1$. On the other hand, the exciting pulse beam $LB_{12}$ is applied to a specimen 3, which produces a phenomenon light beam to be measured, i.e., fluorescence light FL. The fluorescence light FL is passed through a slit $S_2$ and focused by a lens $L_{12}$ so as to be applied to the photocathode $41_2$ of a phenomenon streak tube $4_2$.

Upon application of the reference pulse beam $LB_{11}$ and the fluorescence light FL, the respective photocathodes $41_1$ and $41_2$ emit photoelectrons. In general, the reference pulse beam is narrow in pulse width and high in intensity. Therefore, the number of the photoelectrons emitted from the photocathode $41_1$ of the reference streak tube $4_1$ is one or several per one light pulse, and accordingly it is unnecessary to apply a single photoncounting system thereto. On the other hand, the single photoncounting system is applied to the phenomenon streak tube $4_2$. To this end, the quantity of light incident on the photocathode $41_2$ is limited, for instance, with an ND filter or the like so that the number of photoelectrons emitted per one light pulse is not more than one.

The single photon-counting system will be described briefly.

Upon reception of one light pulse, the specimen produces the fluorescence light, whereby the photocathode of the streak tube emits one photoelectron. The one photoelectron thus emitted is streak-swept by a sweep voltage synchronous with the light pulse, and is subjected to electron multiplication by the MCP, thus forming an streak image on the phosphor screen. Accordingly, the time position of the streak image corresponds to the period of time which elapses from the time instant the light pulse is applied to the specimen until the latter produces the fluorescence light. The above-described operation is repeatedly carried out, so that data representing the time positions of the streak images are stored. The time position data are used to form a histogram with time on the horizontal axis, and frequency on the vertical axis. With the histogram, a light observation waveform can be obtained as a fluorescence life characteristic.

Similarly as in the case of the conventional streak camera device, the photoelectrons emitted from the photocathodes $41_1$ and $41_2$ are accelera ·d ·treak-swept by the deflecting electrodes $44_1$ and $44_2$, and subjected to electron multiplication by the MCPs $45_1$ and $45_2$, respectively. Accordingly, streak images (a reference streak image and a phenomenon streak image) corresponding to the reference pulse beam $LB_{11}$ and the fluorescence light FL are formed on the phosphor screens $46_1$ and $46_2$ of the reference streak tube $4_1$ and the phenomenon streak tube $4_2$, respectively. It should be noted that the sweep voltages applied respectively to the deflecting electrodes $44_1$ and $44_2$ of the reference and phenomenon streak tubes $4_1$ and $4_2$ are provided by the common sweep circuit 8. Therefore, even when the light emission power of the pulse light source 1 changes resulting in the occurrence of a jitter, the time positions of the reference streak image and the phenomenon streak image are shifted in the same manner, and therefore the difference therebetween is correctly in correspondence to the timing of formation of the phenomenon light.

The gain of the MCP $45_1$ of the reference streak tube $4_1$ is set lower than that of the MCP $45_2$ of the phenomenon streak tube $4_2$, because the fluorescence light FL is much weaker than the reference pulse beam $LB_{11}$. The phenomenon streak tube $4_2$ may be a photon-counting type streak tube. The photon-counting type streak tube incorporates a plurality of (generally two to five) MCPs or curved MCPs, and shows a high electron multiplication factor with respect to a single photoelectron and an excellent pulse height characteristic. When compared with an ordinary streak tube, the photon-counting type streak is high in gain and accordingly high in detection efficiency, and it is uniform in pulse height characteristic and accordingly high in S/N ratio. Furthermore, if it is so designed that a threshold level is set with a reading device and only outputs higher than the level are counted, then the effect of the noise or drift can be reduced.

The reference streak image formed on the phosphor screen $46_1$ of the reference streak tube $4_1$ is applied through a lens $L_{21}$ to a reference light beam incident position detecting unit $9_1$, where it is converted into an electrical signal (or photocurrent) corresponding to the incident position (or gravity center position). The electrical signal is supplied to a reference table $10_1$. The reference table is to correct the non-linearity of the streak sweep. The data on the time position of the reference streak image corrected is applied to an arithmetic unit 11. On the other hand, the phenomenon streak image formed on the phosphor screen $46_2$ of the phenomenon streak tube $4_2$ is applied through a lens $L_{22}$ to a phenomenon light beam incident position detecting unit $9_2$, where it is converted into a signal corresponding to the incident position of the fluorescence light FL (signal photon). The signal is supplied to a phenomenon table $10_2$, which is similar in operation to the above-described reference table $10_1$. The data on the time position of the phenomenon streak image corrected is also supplied to the arithmetic unit 11.

The arithmetic unit operates to obtain the difference in time position between the reference streak image and the phenomenon streak image, and the difference thus obtained is supplied to an analyzing unit 12. It is assumed that the power of the pulse light source 1 changes, whereby the output timing of the photodetector 5 is changed, and accordingly the streak sweep timing of the sweep circuit 8 is changed. In this case, in the phenomenon streak tube $4_2$, the time position basis of the phenomenon streak image is changed. At the same time, in the reference streak tube $4_1$, the same change occurs with the reference streak image. Hence, the difference in time position between the reference streak image and the phenomenon streak image corresponds exactly to the period of time which elapses from the application of the exciting pulse beam $LB_{12}$ until the production of the phenomenon light beam, i.e., the fluorescence light FL.

The above-described one cycle of operations is repeatedly carried out by outputting the pulse laser beam FLB from the pulse light source 1 over a plurality of periods, and the results of the operations are applied to the analyzing unit 12, where they are integrated. As a result of the integration, the probability distribution of the time differences is obtained, whereby the phenomenon light waveform is obtained. The phenomenon light waveform thus obtained is displayed on a display unit (or CRT (cathode ray tube)) attached to the analyzing unit 12.

In the above-described embodiment, the streak tube encounters a jitter during sweep. However, since the two streak tubes are swept with one and the same sweep voltage, the output of the arithmetic unit 11 is not affected by the jitter at all if the sweep is performed completely linearly and the light beam incident position detecting units $9_1$ and $9_2$ have no figure distortion. In practice, however, the sweep voltage is not linear, and the light beam incident position detecting units $9_1$ and $9_2$ suffer from figure distortion. Therefore, if the positions of the streak images on the phosphor screens $46_1$ and $46_2$ are shifted by the jitter, then the output of the arithmetic unit 11 will have an error, even if the signals thereto are completely equal in time difference to each other. However, this difficulty may be eliminated by measuring the error which attributes to the incident position on the phosphor screen in advance, because the nonlinearity of the sweep voltage and the figure distortion of the light beam incident position detecting units $9_1$ and $9_2$ are reproducibly constant. Thus, the streak camera device of the invention is provided with the tables $10_1$ and $10_2$ following the light beam position detecting units $9_1$ and $9_2$.

Now, a streak camera device, which is a second embodiment of the invention, will be described with reference to FIG. 2.

Figure 2:
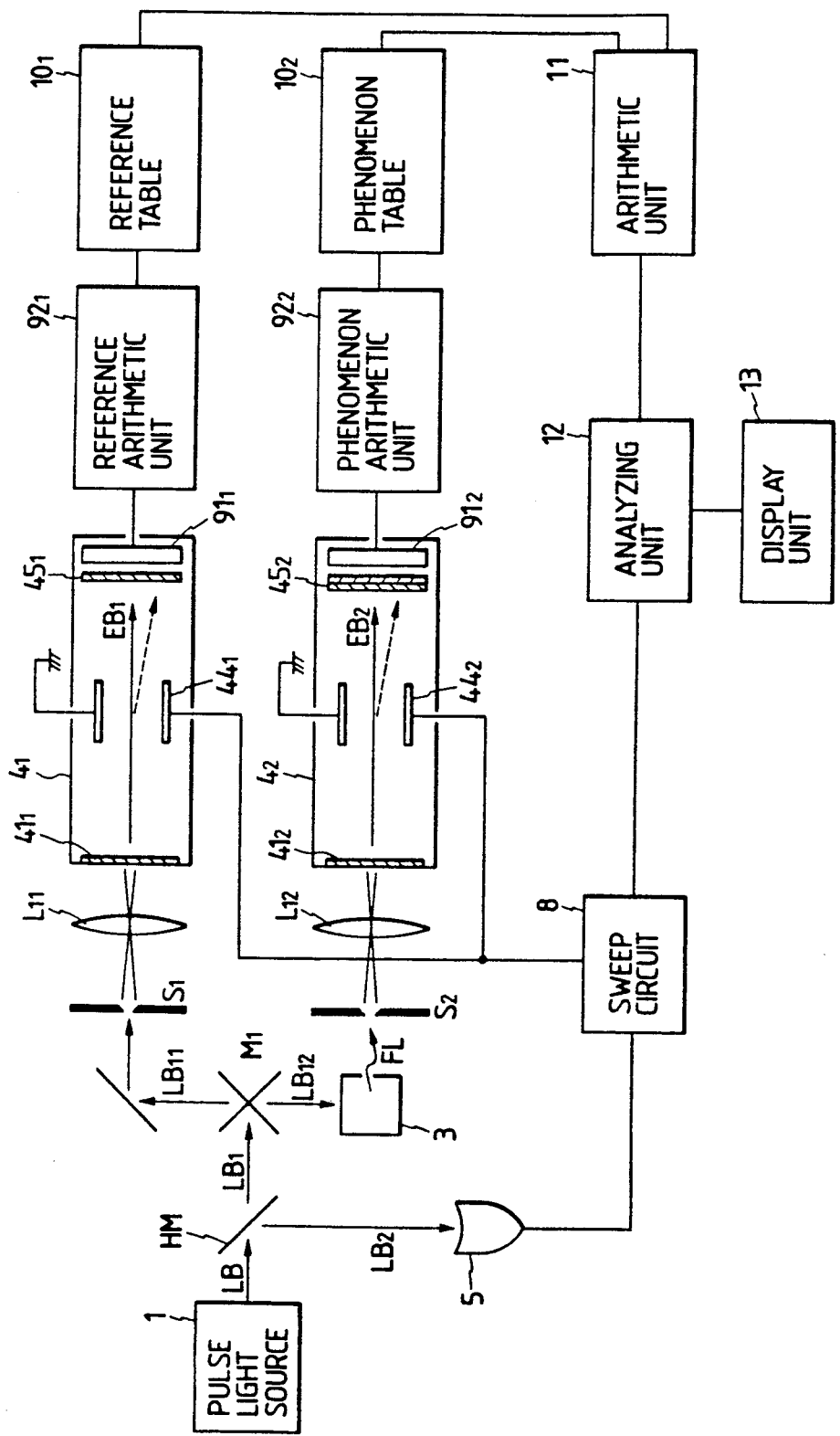
FIG. 2 is an explanatory diagram, partly as a block diagram, showing the arrangement of a streak camera device which is a second embodiment of the invention.

The streak camera device shown in FIG. 2 is different from the device shown in FIG. 1 only in that, in the reference streak tube $4_1$ and the phenomenon streak tube $4_2$, electron incident position detecting elements $91_1$ and $91_2$ are provided instead of the phosphor screens $46_1$ and $46_2$, respectively, and the outputs of the electron incident position detecting elements $91_1$ and $91_2$ which correspond to the incident positions are applied through a reference arithmetic unit $92_1$ and a phenomenon arithmetic unit $92_2$ to the reference table $10_1$ and the phenomenon table $10_2$, respectively.

The electron incident position detecting elements $91_1$ and $91_2$ may be, for instance, linear image sensors, two-dimensional solid-state image pickup elements, or position-sensitive detectors. The position sensitive detecting element may be, for instance, a position-sensitive device (PSD) which is a semiconductor chip with a p-n junction, or a uniform resistance element called "resistive anode". In the streak camera device shown in FIG. 2, in the reference streak tube $4_1$ and the phenomenon streak tube $4_2$ the electron incident position detecting elements $91_1$ and $91_2$ are provided instead of the phosphor screens $46_1$ and $46_2$, respectively, as was described above. However, the detecting elements $91_1$ and $91_2$ may be provided outside the streak tubes $4_1$ and $4_2$ in such a manner that they are positioned behind the phosphor screens $46_1$ and $46_2$, respectively.

Figure 3:
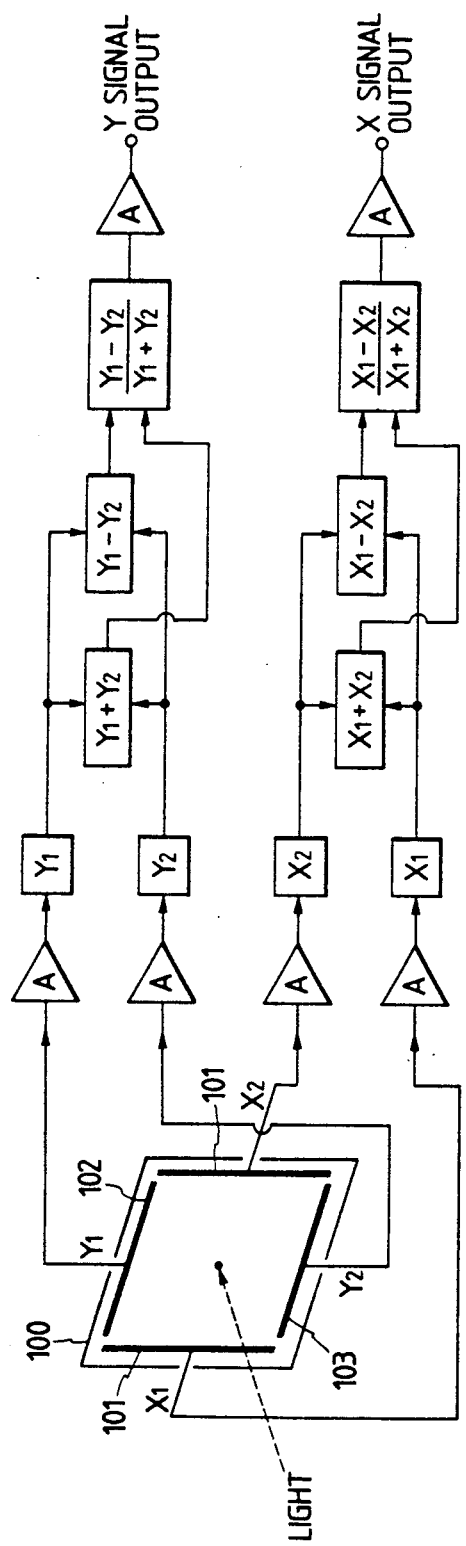
FIG. 3 is an explanatory diagram, partly as a block diagram, showing an arithmetic circuit for the outputs of a PSD.

In general, the number of photoelectrons applied to the MCP of a streak tube is increased by $10^6$ times by the MCP, and the photoelectrons thus increased in number, being accelerated by a high voltage provided between the output side of the MCP and the phosphor screen, are caused to collide with the latter, thus being increased by $10^8$ times in total so as to be converted into light. The image on the phosphor screen is projected onto, for example, the light receiving surface of the PSD, where it is converted into an electron charge signal. In the case of FIG. 3, a PSD 100 has four signal electrodes 101, 102, 103 and 104 along the four sides. Each of the signal electrodes provides a charge signal which is inversely proportional to the resistance, i.e., the distance between the incident position of a light beam and the signal electrode. The output signals of the signal electrodes are subjected to addition, subtraction and division in a circuit as shown in FIG. 3, so that the position of the light beam, i.e., the position of the photoelectrons applied to the MCP is obtained. In FIG. 3, reference character A designates amplifiers; and $X_1$, $X_2$, $Y_1$ and $Y_2$, integrators.

Figure 4:
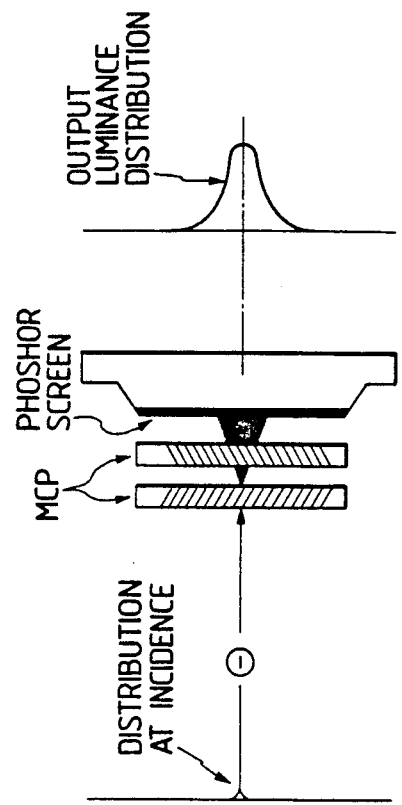
FIG. 4 is an explanatory drawing showing the divergence of photoelectrons.

In practice, the photoelectrons applied to the MCP will diverge while being amplified by the MCP (moving from the MCP to the phosphor screen) as shown in FIG. 4. However, with the electron incident position detecting element using a position-sensitive detector such as a PSD, even if the image on the phosphor screen is expanded, the gravity center position thereof can be obtained with high accuracy. The above-described PSD is a two-dimensional one. Therefore, two-dimensional data with respect to the time axis (Y) and space axis (X) (which is defined by the incident positions of light beams to the incident slits $S_1$ and $S_2$ of the streak camera) are measured in this case.

The resistive anode type position-sensitive detector, being a uniform resistance element, is not sensitive to light. If the detectors (the detecting elements $9_1$ and $9_2$)

are built in the streak tubes as shown in FIG. 2, the resistive anode type position-sensitive detector may be employed. The above-described PSD is sensitive to both light incidence and electron incidence.

In the case where the linear image sensor or the two-dimensional solid-state image pickup element is employed as the electron incident position detecting element, unlike in the case of the position-sensitive detector, it is impossible to automatically obtain the gravity center position. Therefore, in order to perform the measurement with high accuracy, it is preferable to perform an operation of obtaining the gravity center from the output video signal. In the case of the reference streak tube $4_1$, a plurality of incident photoelectrons are provided, and therefore with only one MCP the position measurement can be achieved with sufficiently high S/N ratio. In this case, since the divergence of electrons is considerably small with one MCP, it is unnecessary to calculate the gravity center position with high accuracy; that is, all that is necessary may be to obtain the pulse peak position.

Now, a streak camera device, which is a third embodiment of the invention, will be described.

Figure 5:
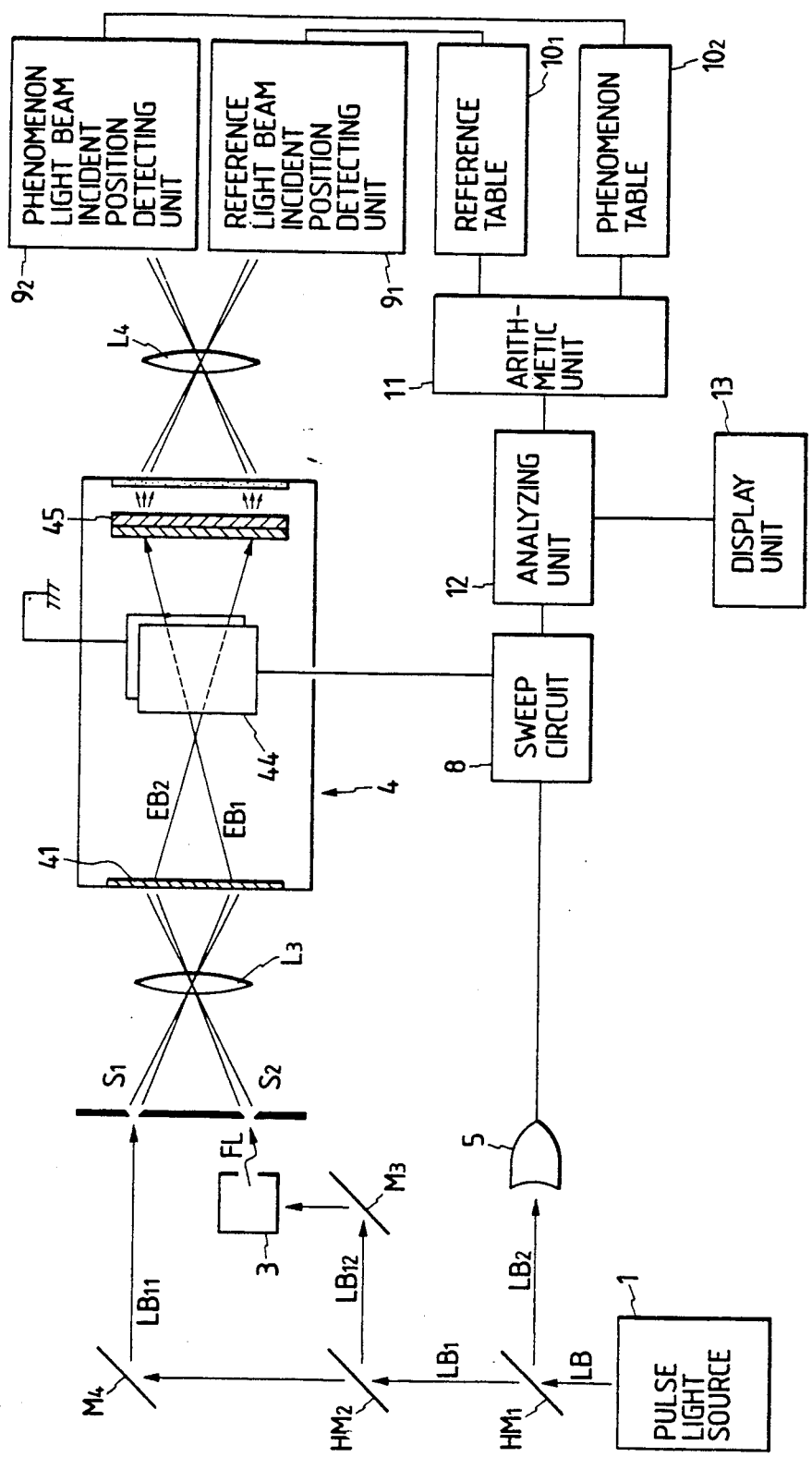
FIG. 5 is an explanatory diagram, partly as a block diagram, showing a streak camera device which is a third embodiment of the invention.
Figure 6:
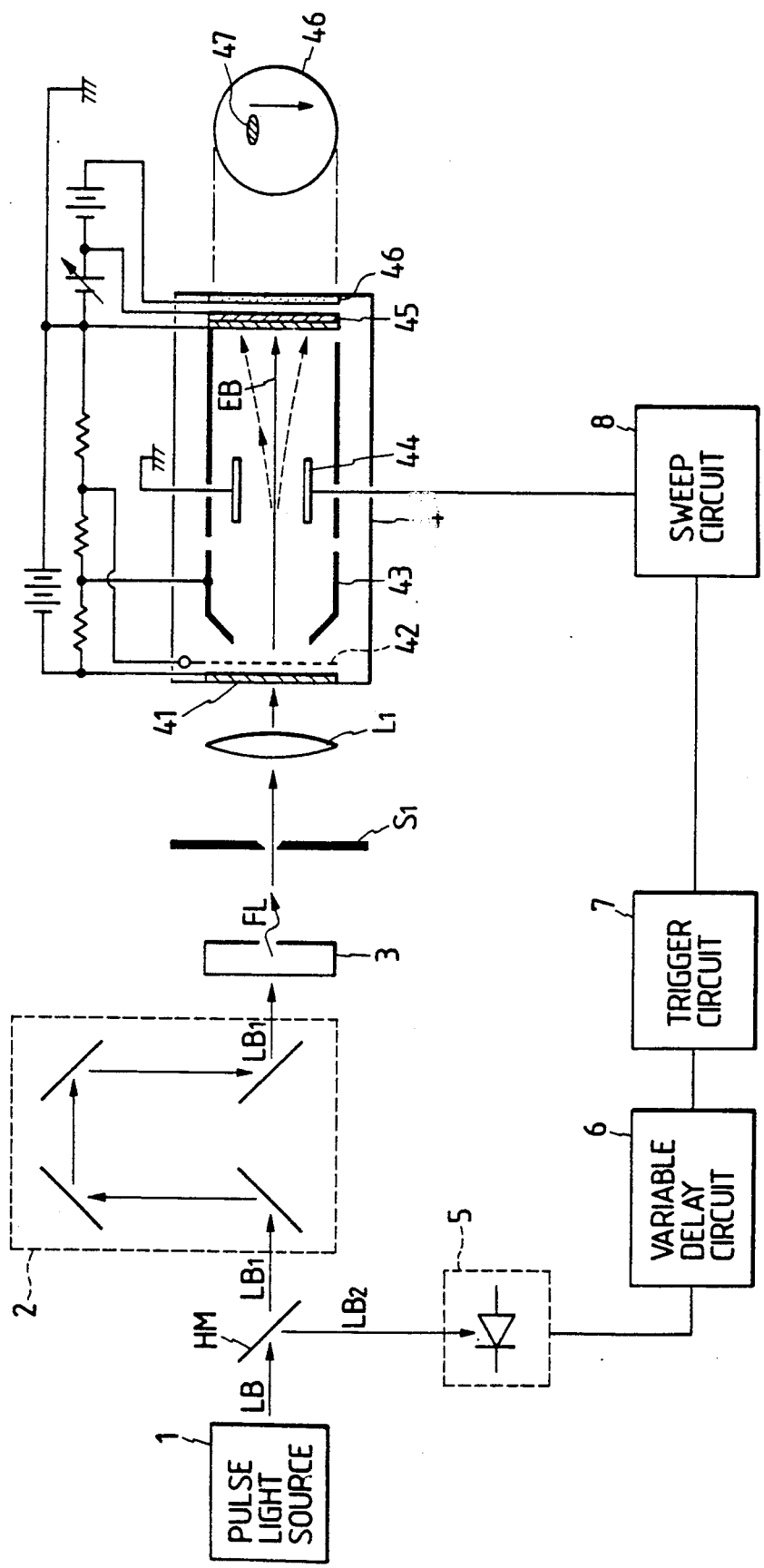
FIG. 6 is an explanatory diagram, partly as a block diagram, showing a conventional streak camera device.
Figure 7A:
FIG. 7($a$) through 7($c$) are an explanatory diagram for a description of the occurrence of a jitter caused by the change in power of a light output.
Figure 7B:
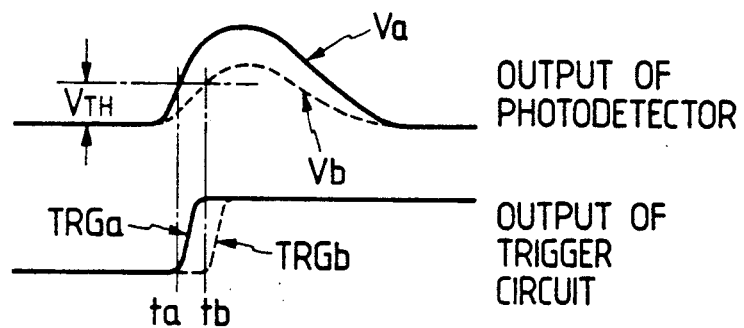
Figure 7C:
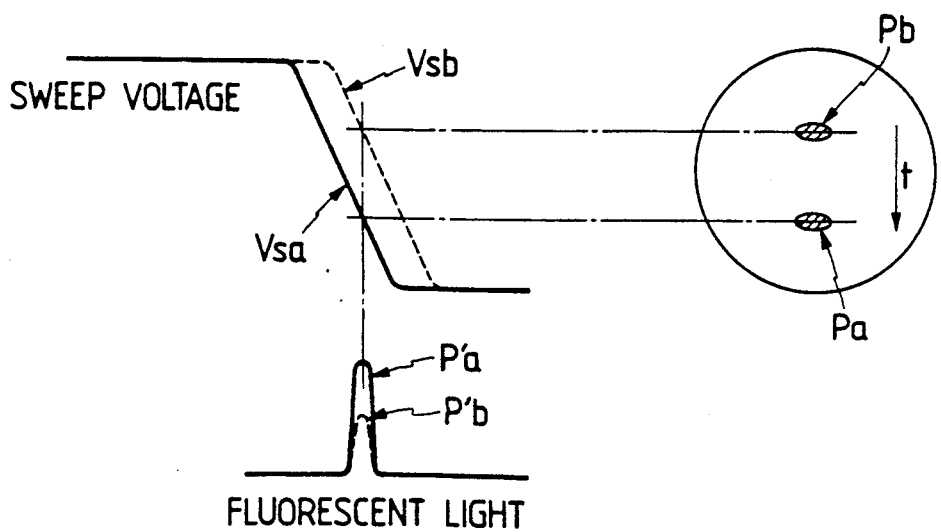

FIG. 5 is an explanatory diagram, partly as a block diagram, showing the streak camera device. The streak camera device shown in FIG. 5 is different from the device shown in FIG. 1 in that only one streak tube 4 is provided for both a phenomenon light beam and a reference light beam. The photoelectrons $EN_1$ and $EB_2$ produced by the reference pulse beam $LB_{11}$ and the fluorescence light FL, respectively, are passed through the same deflecting electrodes 44 so that they are commonly swept. Therefore, similarly as in the first embodiment of the invention, the time measurement can be achieved with high accuracy from the difference in time position between the reference streak image and the phenomenon streak image. In the third embodiment, an optical system for splitting the pulse laser beam LB from the pulse light source 1 into the reference pulse beam $LB_{11}$, the exciting pulse beam $LB_{12}$, and the trigger pulse beam $LB_2$ is different from the above-described one; however, the former is not fundamentally different from the latter. The third embodiment may be so modified that a detector such as the PSD or the linear image sensor is arranged inside or outside the streak tube 4.

Furthermore, in the above-described embodiments, the trigger signal is obtained from the trigger pulse beam $LB_2$ which is formed by splitting the pulse laser beam LB. However, in the case where the pulse light source 1 is a semiconductor laser, the trigger signal may be obtained from its drive signal.

As was described above, according to the invention, even when a drift or jitter occurs because of the change in power of the pulse light source itself or the change in the light source drive circuit, both the phenomenon streak system and the reference streak system are affected thereby in the same manner, and the difference between the resultant effects is obtained. Thus, the photon-counting type streak camera device according to the invention is considerably high in time resolution.

What is claimed is:

1. A streak camera device in which an operation of detecting a phenomenon light beam which a specimen produces upon reception of a pulse light beam generated repeatedly with a predetermined frequency is performed a plurality of times according to the predetermined frequency, to obtain a probability distribution of production timing of the phenomenon light beam, thereby to measure a time waveform thereof, comprising:
   light splitting means for splitting said pulse light beam into a reference light beam and an exciting light beam to be applied to said specimen;
   trigger signal generating means for producing a trigger signal synchronous, with said reference light beam;
   reference streak means for sweeping according to said trigger signal photoelectrons which are produced upon incidence of said reference light beam;
   phenomenon streak means for sweeping according to said trigger signal photoelectrons which are produced upon incidence of said phenomenon light beam which said specimen emits upon reception of said exciting light beam;
   reference position detecting means for detecting a time position of a reference streak image formed by said reference streak means;
   phenomenon position detecting means for detecting a time position of a phenomenon streak image formed by said phenomenon streak means; and
   arithmetic means for calculating said production timing of said phenomenon light beam from a difference between an output of said phenomenon position detecting means and an output of said reference position detecting means.

2. A streak camera device as claimed in claim 1, wherein said phenomenon streak means comprises a high gain photon-counting type streak tube.

3. A streak camera device as claimed in claim 1, wherein one and the same streak tube functions as said reference streak means and said phenomenon streak means.

4. A streak camera device as claimed in claim 1, wherein each of said reference and phenomenon position detecting means comprises a linear image sensor.

5. A streak camera device as claimed in claim 1, wherein each of said reference and phenomenon position detecting means comprises a two-dimensional solid-state image pickup element.

6. A streak camera device as claimed in claim 1, wherein each of said reference and phenomenon position detecting means comprises a position-sensitive detector.

7. A streak camera device as claimed in claim 1, wherein a detecting element of each of said reference and phenomenon position detecting means is incorporated in said reference or phenomenon streak means so as to receive said photoelectrons.

* * * * *